(12) United States Patent
Tsao

(10) Patent No.: US 7,022,654 B2
(45) Date of Patent: Apr. 4, 2006

(54) COMPOSITIONS AND METHODS FOR CLEANING CONTACT LENSES

(75) Inventor: Fu-Pao Tsao, Lawrenceville, GA (US)

(73) Assignee: Novartis AG, Basel (CH)

( * ) Notice: Subject to any disclaimer, the term of this patent is extended or adjusted under 35 U.S.C. 154(b) by 926 days.

(21) Appl. No.: 09/963,972

(22) Filed: Sep. 26, 2001

(65) Prior Publication Data

US 2002/0141899 A1 Oct. 3, 2002

Related U.S. Application Data

(60) Provisional application No. 60/236,254, filed on Sep. 28, 2000.

(51) Int. Cl.
*C11D 43/00* (2006.01)
*C11D 3/395* (2006.01)
*A61L 2/18* (2006.01)

(52) U.S. Cl. .................. 510/115; 510/112; 510/372; 134/26; 134/42; 514/839; 514/840

(58) Field of Classification Search ............ 510/112, 510/115, 372; 134/26, 42; 514/839, 840
See application file for complete search history.

(56) References Cited

U.S. PATENT DOCUMENTS

| | | | |
|---|---|---|---|
| 3,882,036 A | | 5/1975 | Krezanoski |
| 4,440,662 A | | 4/1984 | Tsuzuki et al. ............ 252/106 |
| 4,510,065 A | | 4/1985 | Sherman ................... 252/106 |
| 4,740,533 A | * | 4/1988 | Su et al. |
| 4,812,173 A | * | 3/1989 | Tsao et al. |
| 5,209,865 A | * | 5/1993 | Winterton et al. |
| 5,256,420 A | * | 10/1993 | Tsao et al. |
| 5,288,814 A | * | 2/1994 | Long, II et al. |
| 5,298,182 A | * | 3/1994 | Tsao et al. |
| 5,411,597 A | * | 5/1995 | Tsao et al. |
| 5,411,598 A | * | 5/1995 | Tsao et al. |
| 5,470,568 A | * | 11/1995 | Lee |
| 5,523,012 A | * | 6/1996 | Winterton et al. |
| 5,739,371 A | | 4/1998 | O'Lenick |
| 5,746,972 A | | 5/1998 | Park |
| 5,773,396 A | | 6/1998 | Zhang |
| 5,820,696 A | | 10/1998 | Kimura |
| 5,846,919 A | * | 12/1998 | Tsao et al. |
| 5,965,088 A | | 10/1999 | Lever |
| 6,037,328 A | | 3/2000 | Hu |
| 6,063,745 A | | 5/2000 | Graham |
| 2003/0095945 A1 | * | 5/2003 | Levy et al. |
| 2003/0118550 A1 | * | 6/2003 | Kabanov et al. ............ 424/93.2 |
| 2003/0125211 A1 | * | 7/2003 | Woznica et al. ............ 504/363 |
| 2003/0148913 A1 | * | 8/2003 | Klinkhammer et al. ..... 510/421 |
| 2004/0092102 A1 | * | 5/2004 | Li et al. |

FOREIGN PATENT DOCUMENTS

| | | |
|---|---|---|
| EP | 0 819 968 | 1/1998 |
| EP | 0 855 188 A2 | 7/1998 |
| EP | 0 877 075 A1 | 11/1998 |
| EP | 0 923 950 A2 | 6/1999 |
| EP | 0 958 836 A2 | 11/1999 |
| FR | 2584503 | 1/1987 |
| JP | 09206362 | 8/1997 |
| JP | 63136020 | 6/1998 |
| JP | 11006986 | 1/1999 |
| JP | 11080795 | 3/1999 |
| JP | 10108897 | 4/1999 |
| JP | 10108899 | 4/1999 |
| JP | 11116992 | 4/1999 |
| JP | 1119989 | 7/1999 |
| NL | 9101986 | 6/1993 |
| WO | WO 95/01414 | 1/1995 |
| WO | WO 98/04496 | 2/1998 |
| WO | WO 98/55155 | 12/1998 |
| WO | WO 99/24542 | 5/1999 |

* cited by examiner

*Primary Examiner*—Michael Barr
*Assistant Examiner*—John M Petruncio
(74) *Attorney, Agent, or Firm*—Jian S. Zhou

(57) ABSTRACT

A composition for disinfecting a contact lens comprising an effective disinfecting amount of hydrogen peroxide and a surfactant comprising a copolymer of hydrophobe and hydrophile blocks the structure:

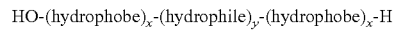

or

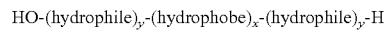

where x and y are integers reflecting the respective hydrophile and hydrophobe blocks of said copolymer; and the hydrophile component of the block copolymer constitutes less than 50 weight percent of the block copolymer. The block copolymer has a Ross-Miles foam height (ASTM designation D-1173-53; 0.1%, at 50° C.) of less than 1 mm.

38 Claims, No Drawings

COMPOSITIONS AND METHODS FOR CLEANING CONTACT LENSES

RELATED APPLICATION

This application claims priority of Provisional Application: 60/236,254, filed Sep. 28, 2000.

BACKGROUND OF THE INVENTION

1. Field of the Invention

This invention relates generally to disinfection and cleaning systems for medical devices. In a preferred embodiment, the invention relates to compositions, methods and articles for simultaneously cleaning and disinfecting contact lenses.

2. Description of the Related Art

Disinfecting solutions for use with contact lenses are well known in the art and the use of such lenses involves a daily disinfecting treatment. Flexible, or soft, contact lenses are generally made from hydrophilic polymers and the hydroxy groups of these lenses attract and retain substantial amounts of water in the plastic which results in difficulties during cleaning and sterilization.

Hydrogen peroxide systems, particularly 3% hydrogen peroxide solutions, emerged as the disinfectant of choice for all types of daily and extended wear hydrogel lenses. The primary reason for its popularity is its rapid kill of microbial contaminants and its non-residual character. After hydrogen peroxide disinfects lenses, it can be converted into innocuous and natural by-products, such as $O_2$ and water, which are compatible with ocular physiology. See Krezanoski et al., "Journal of the American Optometric Association", Vol. 59, Number 3, pages 193–197 (1988).

In general, the hydrogen peroxide systems involve a hydrogen peroxide-containing disinfecting solution into which the contact lenses to be disinfected are placed and allowed to remain for a required period of time. The hydrogen peroxide may (1) oxidize chloride in the bacteria to hypochlorite or (2) decompose into nascent oxygen and hydroxyl radicals, thus providing a germicidal effect. Following the requisite time period a purposeful inactivation of the hydrogen peroxide is conducted, for example, with a platinum catalyst. Following inactivation, the contact lens may be reinserted into the eye.

However, harmful microorganisms, proteins, lipids, and other irritating deposits are not always sufficiently removed by peroxide disinfection alone and the lens should be cleaned and rinsed beforehand. This is typically performed by wetting the lens with a sufficient amount of a lens cleaner (such as CIBA Vision® MiraFlow®) and then rubbing the lens with one's fingers and rinsing the lens with saline. The cleaning step is considered a hassle by some consumers and a peroxide disinfection system that adequately disinfects and cleans without this step (a "no rub-no rinse" regimen) would offer a great improvement in convenience to the user.

U.S. Pat. No. 5,523,012 to Winterton, et al. teaches that the addition of a surface-active agent to a peroxide disinfection solution will enhance the disinfecting properties of the solution. However, the surfactants disclosed are all present in amounts above 0.1% and, because of excessive foaming, are incompatible with the platinum catalyst disc typically used to deactivate hydrogen peroxide in lens disinfection systems.

EP0855188 teaches that glycerol, polyhydric alcohol, and Tween 20 will reduce the rate at which hydrogen peroxide will decompose, thus increasing its disinfecting efficacy. However, there are significant problems with each of these compositions that effectively preclude their use in a contact lens disinfection solution. For instance, glycerol is not stable in 3% hydrogen peroxide and both polyhydric alcohol, such as PVA, and Tween 20 will cause excessive foaming when the solution contacts the catalytic disc and decomposes.

U.S. Pat. No. 5,746,972 to Park, et al. teaches compositions and methods for disinfecting and cleaning contact lenses include a liquid medium containing hydrogen peroxide and a solid ethylene oxide/propylene oxide block copolymer surfactant having at least 70% by weight polyethylene oxide. The hydrogen peroxide is degraded by a catalase released into the solution and causes "a reduced amount of foam." However, such compositions cause excessive foaming when a platinum catalyst is used to decompose the hydrogen peroxide.

In an effort to provide greater convenience, new regimens have been developed. These system provides the benefit of combined "daily" cleaning and disinfection in one non-peroxide solution, wherein the same solution may be directly used in combination with enzymatic cleaners, thus reducing the number of steps and components required for effective lens cleaning and disinfection. However, no such "one-step" regimen exists for hydrogen peroxide systems.

Therefore, it would be advantageous to provide peroxide contact lens disinfection solutions that overcome one or more of these problems.

SUMMARY OF THE PRESENT INVENTION

The present invention includes methods for treating contact lenses and compositions for the same. It has been surprisingly found that a composition for disinfecting a contact lens comprising an effective disinfecting amount of hydrogen peroxide and a surfactant comprising a low-foaming or non-foaming copolymer of hydrophobe and hydrophile blocks having the structure:

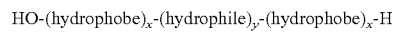

or

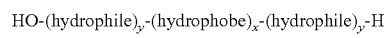

have outstanding disinfection efficacy, even when used without an additional rub and rinse step. The designations x and y are integers reflect the respective hydrophile and hydrophobe blocks of said copolymer; and the hydrophile component of the block copolymer constitutes less than 50 weight percent of the block copolymer. In a preferred embodiment, the surfactant is a polyoxyethylene/polyoxypropylene block copolymer having a Ross-Miles foam height of less than 1 mm at 0.1% and 50° C. Furthermore, the solutions described herein are compatible with common peroxide decomposition catalysts. Thus, the invention represents a significant improvement in the disinfection of contact lenses, particularly by providing peroxide solutions suitable for use in a "no rub-no rinse" regimen of lens care.

The invention also involves a method for disinfecting contact lenses comprising contacting a contact lens with a liquid medium containing hydrogen peroxide and polyoxyethylene/polyoxypropylene block copolymer having a Ross-Miles foam height of less than 1 mm at 0.1% and 50° C. to thereby disinfect the contact lens.

These and other aspects and advantages of the present invention will become apparent in the detailed description, examples, and claims.

DETAILED DESCRIPTION OF THE PREFERRED EMBODIMENT

The present invention is directed to a composition, in the form of an aqueous solution containing hydrogen peroxide and a block copolymer of hydrophobe and hydrophile blocks, which are preferably ethylene oxide and propylene oxide; and a method of using the solution for disinfecting and/or preserving contact lenses, especially soft contact lenses. The disinfecting solutions of the present invention are effective against a wide spectrum of microorganisms, including but not limited to *Staphylococcus aureus, Pseudomonas aeruginosa, Serratia marcescens, Candida albicans*, and *Fusarium solani*.

A disinfecting solution is generally defined as a contact lens care product containing one or more active ingredients (for example, anti-microbial agents and/or preservatives) in sufficient concentrations to destroy harmful microorganisms on the surface of a contact lens within the recommended minimum soaking time. The recommended minimum soaking time is included in the package instructions for use of the disinfecting solution. The present solution, in combination with its container or bottle and packaging, including instructions for use, may be considered a novel and improved kit, package, or system for the care of contact lenses.

The term "soft lens" means a lens having a proportion of hydrophilic repeat units such that the water content of the lens during use is at least 20% by weight. The term "soft contact lens" as used herein generally refers to those contact lenses which readily flex under small amounts of force. Typically, soft contact lenses are formulated from polymers having a certain proportion of repeat units derived from hydroxyethyl methacrylate and/or other hydrophilic monomers, typically crosslinked with a crosslinking agent. In contrast, conventional "hard contact lenses," which cover only a part of the cornea of the eye, usually consist of poly(methyl methacrylate) crosslinked with ethylene glycol dimethacrylate or the like, and conventional rigid gas permeable lenses (RGP) typically consists of monomers containing silicon that result in a more oxygen-permeable material.

By the term "ophthalmically safe" with respect to a contact-lens solution is meant that a contact lens treated with the solution is safe for direct placement on the eye without rinsing, that is, the solution is safe and sufficiently comfortable for daily contact with the eye via a contact lens. An ophthalmically safe solution has a tonicity and pH that is compatible with the eye and comprises materials, and amounts thereof, that are non-cytotoxic according to international ISO standards and U.S. FDA regulations.

The term "compatible with the eye" means a solution that may be in intimate contact with the eye for an extended period of time without significantly damaging the eye and without significant user discomfort.

The term "disinfecting solution" means a solution containing one or more microbiocidal compounds, that is effective for reducing or substantially eliminating the presence of an array of microorganisms present on a contact lens, which can be tested by challenging a solution or a contact lens after immersion in the solution with specified inoculums of such microorganisms. The term "disinfecting solution" as used herein does not exclude the possibility that the solution may also be useful for a preserving solution or that the disinfecting solution may additionally be useful for daily cleaning, rinsing, and storage of contact lenses.

The term "cleaning" means that the solution contains one or more active ingredients in sufficient concentrations to loosen and remove loosely held lens deposits and other contaminants on the surface of the article to be cleaned. While not necessary with the present invention, a user may wish to use the solutions of the present invention in conjunction with digital manipulation (for example, manual rubbing of the lens with a solution) or with an accessory device that agitates the solution in contact with the lens, for example, a mechanical cleaning aid.

A solution that is useful for cleaning, chemical disinfection, storing, and rinsing an article, such as a contact lens, is referred to herein as a "multi-purpose solution." Such solutions may be part of a "multi-purpose solution system" or "multi-purpose solution package." The procedure for using a multi-purpose solution, system or package is referred to as a "multi-functional disinfection regimen." Multi-purpose solutions do not exclude the possibility that some wearers, for example, wearers particularly sensitive to chemical disinfectants or other chemical agents, may prefer to rinse or wet a contact lens with a another solution, for example, a sterile saline solution prior to insertion of the lens. The term "multi-purpose solution" also does not exclude the possibility of periodic cleaners not used on a daily basis or supplemental cleaners for removing proteins, for example enzyme cleaners, which are typically used on a weekly basis.

"Molecular weight" of a polymeric material, as used herein, refers to the number-average molecular weight unless otherwise specifically noted or unless testing conditions indicate otherwise.

The solution of the invention contains hydrogen peroxide in a concentration that is suitable for disinfecting purposes, preferably about 0.5% to about 6%, more preferably about 2% to about 6% by weight, most preferably between 3% and 4%, or about 3% by weight.

Suitable surfactants can be generally described as block copolymers of a hydrophile and hydrophobe terminated in either primary or secondary hydroxyl groups. A first example of such surfactants are polyoxyethylene/polyoxypropylene condensation polymers terminated in primary hydroxyl groups. They may be synthesized by first creating a hydrophobe of desired molecular weight by the controlled addition of propylene oxide to the two hydroxyl groups of propylene glycol. In the second step of the synthesis, ethylene oxide is added to sandwich this hydrophobe between hydrophile groups. Such block copolymers can be obtained commercially from the BASF Corporation under the trademark PLURONIC®.

A second example of such surfactants are polyoxyethylene/polyoxypropylene condensation polymers terminated in secondary hydroxyl groups. They may be synthesized by first creating a hydrophile (polyoxyethylene) of desired molecular weight by the controlled addition of ethylene oxide to ethylene glycol. In the second step of the synthesis, propylene oxide is added to create hydrophobic blocks on the outside of the molecule. Such block copolymers can be obtained commercially from the BASF Corporation under the trademark PLURONIC® R.

The preferred surfactant is a block copolymer of ethylene oxide and propylene oxide having the formula:

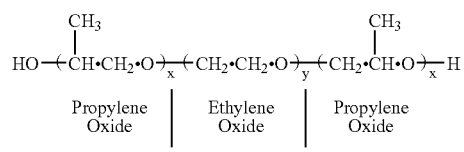

wherein x and y are integers from 1 to 350 reflecting the respective polyethylene oxide and polypropylene oxide blocks of said copolymer. The polyoxyethylene component of the block copolymer constitutes from 10 to 90 weight percent of the block copolymer. Preferably, the polyoxyethylene component of the block copolymer constitutes from 10 to 50 weight percent of the block copolymer. In another preferred embodiment of the present invention, the polyoxyethylene component of the block copolymer constitutes less than 50 weight percent of the block copolymer. Most preferably, the polyoxyethylene component of the block copolymer constitutes about 40 weight percent of the block copolymer.

Surfactants having a total molecular weight of 1000 to about 20000 are preferred. More preferred are those surfactants having a molecular weight of 1200 to 3100. Most preferred are those surfactants having a molecular weight of about 2650.

The amount of surfactant component varies over a wide range depending on a number of factors, for example, the specific surfactant or surfactants being used, the other components in the composition and the like. Often the amount of surfactant is in the range of about 0.005% or about 0.01% to about 0.1% or about 0.5% or about 0.8% (w/v). Preferably, the surfactant is present in an amount less than 0.2%; and most preferably less than 0.1%.

The sequence and percent distribution of hydrophobic and hydrophilic segments in these block copolymers leads to important differences in surfactant properties. The surfactant is preferably a liquid at 20° C. The molecular weight of the polyoxypropylene block is preferably from about 1200 and about 3100. Preferably, molecular weight of the polyoxypropylene block is from about 1000 and about 2500. Most preferably, the molecular weight of the polyoxypropylene block is approximately 1700. Specific examples of PLURONIC® surfactants that are satisfactory include: PLURONIC® L42, PLURONIC® L43, and PLURONIC® L61. Specific examples of PLURONIC® R surfactants that are satisfactory include: PLURONIC® 31R1, PLURONIC® 31R2, PLURONIC® 25R1, PLURONIC® 17R1, PLURONIC® 17R2, PLURONIC® 12R3. Particularly good results are obtained with PLURONIC® 17R4 surfactant.

The PLURONIC® letter-number combinations are used to identify the various products of the series. The alphabetical designation explains the physical form of the product: 'L' for liquids, 'P' for pastes, 'F' for solid forms (all at 20° C.). The first digit (two digits in a three-digit number) in the numerical designation, multiplied by 300, indicates the approximate molecular weight of the hydrophobe (polypropylene oxide). The last digit, when multiplied by 10, indicates the approximate polyethylene oxide content in the molecule in percent.

The letter 'R' found in the middle of the designation of the PLURONIC® R series signifies that this product has a reverse structure compared to the PLURONIC® products, i.e., the hydrophile (ethylene oxide) is sandwiched between the propylene oxide blocks. The numeric designation preceding the 'R', when multiplied by 100, indicates the approximate molecular weight of the propylene oxide block. The number following the 'R', when multiplied by 10, indicates the approximate weight percent ethylene oxide in that product.

When selecting the structure of a block copolymer surfactant, it is important to select those that cause very low or no foaming because surfactants tend to cause excessive foaming when oxygen is generated by the decomposition of the hydrogen peroxide upon contact with the catalytic disk.

While not wishing to be limited by a particular theory of action, it is suspected that the block copolymer surfactants of the present invention provide defoaming/antifoaming action by forming an insoluble monolayer at the air/water interface of the foam. For this reason, the defoaming/antifoaming activity of a block copolymer is a function of both the cloud point of the copolymer and the use temperature. To select an effective defoamer/antifoamer, one should choose a block copolymer whose cloud point is lower than the intended use temperature.

Block copolymers with low ethylene oxide content are the most effective defoamers. Within each series of block copolymer products, defoaming performance increases as ethylene oxide content decreases and molecular weight increases.

The tendency of a surfactant to create and/or sustain foam is measured according to the Ross-Miles test protocol ASTM designation D-1173-53 (0.1%, at 50° C.). Those block copolymers with foam heights less than 1 mm, and most preferably about 0, are suitable for use in the present invention.

It is to be noted that the surfactant of the hydrogen peroxide solution may be only one surfactant of the type described above or a mixture of two or more surfactants, with the proviso that no mixture of surfactants has a foam height greater than 1 mm as measured by ASTM designation D-1173-53.

The composition of the present invention preferably contains a hydrogen peroxide stabilizer. Preferably, the stabilizer is a diphosphonic acid alkanol as disclosed in U.S. Pat. No. 4,812,173. The most preferred stabilizer is diethylene triamine penta-(methylenephosphonic acid) or a physiologically compatible salt thereof. This compound is manufactured by Solutia under the name DEQUEST® 2060. The stabilizer is preferably present in the solution in an amount between about 0.001 and about 0.03% by weight of the composition, and most preferably between about 0.006 and about 0.0120% by weight of the solution. Stabilization of hydrogen peroxide in contact lens disinfection systems is described in more detail in U.S. Pat. Nos. 4,812,173 and 4,889,689, both incorporated herein by reference.

If desired, additional conventional stabilizers may be employed in conjunction with or in place of the diethylene triamine penta-(methylenephosphonic acid) if it is compatible with the material to be sterilized. Some conventional stabilizers are not compatible with the polymers typically found in contact lenses (e.g., sodium stannate), and should therefore, only be used with materials which would not be adversely affected by stannate stabilizers.

The composition of the present invention preferably contains a buffer. The buffer maintains the pH preferably in the desired range, for example, in a physiologically acceptable range of about 4 or about 5 or about 6 to about 8 or about 9 or about 10. In particular, the solution preferably has a pH in the range of about 5.5 to about 8. The buffer is selected from inorganic or organic bases, preferably basic acetates, phosphates, borates, citrates, nitrates, sulfates, tartrates, lactates, carbonates, bicarbonates and mixtures thereof, more preferably basic phosphates, borates, citrates, tartrates, carbonates, bicarbonates and mixtures thereof. Typically, it is present in an amount of 0.001% to 2%, preferably 0.01% to 1%; most preferably from about 0.05% to about 0.30%.

The buffer component preferably includes one or more phosphate buffers, for example, combinations of monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$), and potassium monobasic phosphate ($KH_2PO_4$).

The solutions of the present invention preferably include an effective amount of a tonicity component to provide the liquid medium with the desired tonicity. Such tonicity components may be present in the solution and/or may be introduced into the solution. Among the suitable tonicity adjusting components that may be employed are those conventionally used in contact lens care products, such as various inorganic salts. Sodium chloride and/or potassium chloride and the like are very useful tonicity components. The amount of tonicity component included is effective to provide the desired degree of tonicity to the solution. Such amount may, for example, be in the range of about 0.4% to about 1.5% (w/v). If a combination of sodium chloride and potassium chloride is employed, it is preferred that the weight ratio of sodium chloride to potassium chloride be in the range of about 3 to about 6 or about 8. The preferred tonicity component is sodium chloride present in the range of 0.50% to 0.90%.

Typical tonicity builders for use in the invention include suitable water soluble salts compatible with ocular tissue, preferably alkali or alkali earth metal halide, sulfates, nitrates, carbonates, borates, and phosphates, more preferably sodium or potassium chloride. The tonicity builder is present in an amount sufficient to provide a tonicity of the dosage regimen of 50 to 400 mosmol/kg, most preferably 250 to 350 mosmol/kg. When non-contact lens cleaning is the desired use, the tonicity builder may also be absent or in even greater amounts than set forth above.

Methods for treating a contact lens using the herein described compositions are included within the scope of the invention. Such methods comprise contacting a contact lens with such a composition at conditions effective to provide the desired treatment to the contact lens.

The contacting temperature is preferred to be in the range of about 0° C. to about 100° C., and more preferably in the range of about 10° C. to about 60° C. and still more preferably in the range of about 15° C. to about 37° C. Contacting at or about ambient temperature is very convenient and useful. The contacting preferably occurs at or about atmospheric pressure. The contacting preferably occurs for a time in the range of about 5 minutes or about 1 hour to about 12 hours or more.

The contact lens can be contacted with the solution by immersing the lens in the solution. Although not necessary, the solution containing the contact lens can be agitated, for example, by shaking the container containing the solution and contact lens, to at least facilitate removal of deposit material from the lens.

The solutions and methods of the present invention may be used in conjunction with enzymes to remove debris or deposit material from the contact lens as the solutions of the present invention have no negative effect on the proteolytic activity of enzymes, such as UNIZYME®. After such contacting step, the contact lens optionally may be manually rubbed with saline, or even rinsed without rubbing, to remove further deposit material from the lens. The cleaning method can also include rinsing the lens substantially free of the liquid aqueous medium prior to returning the lens to a wearer's eye.

The following non-limiting examples illustrate certain aspects of the present invention.

EXAMPLE 1 (PRIOR ART)

A quantity of the following liquid composition is prepared by blending together the individual ingredients (in g).

| | |
|---|---|
| Hydrogen peroxide | 35.0 |
| Sodium Phosphate, Monobasic (monohydrate) | 0.072 |
| Sodium Phosphate, Dibasic (Anhydrous) | 0.622 |
| DEQUEST ® 2060 | 0.120 |
| Sodium Chloride | 8.655 |
| USP Purified Water | QS to 1 liter |

The resulting solution is an aqueous solution containing 3.5% hydrogen peroxide; 0.007% sodium phosphate, monobasic (monohydrate); 0.062% sodium phosphate, dibasic (anhydrous); 0.012% DEQUEST® 2060; and 0.866% sodium chloride.

EXAMPLE 2

A quantity of the following liquid composition is prepared by blending together the individual ingredients (in g).

| | |
|---|---|
| Hydrogen peroxide | 35.0 |
| Sodium Phosphate, Monobasic (monohydrate) | 0.772 |
| Sodium Phosphate, Dibasic (Anhydrous) | 1.555 |
| DEQUEST ® 2060 | 0.120 |
| Sodium Chloride | 7.900 |
| PLURONIC ® 17R4 | 0.500 |
| USP Purified Water | QS to 1 liter |

The resulting solution is an aqueous solution containing 3.50% hydrogen peroxide; 0.077% sodium phosphate, monobasic (monohydrate); 0.156% sodium phosphate, dibasic (anhydrous); 0.012% DEQUEST® 2060; 0.79% sodium chloride; and 0.05% PLURONIC® 17R4.

EXAMPLE 3

A solution was prepared in the same manner as Example 2, except the amount of PLURONIC® 17R4 was increased to 1.0 g.

The resulting solution is an aqueous solution containing 3.50% hydrogen peroxide; 0.077% sodium phosphate, monobasic (monohydrate); 0.156% sodium phosphate, dibasic (anhydrous); 0.012% DEQUEST® 2060; 0.79% sodium chloride; and 0.10% PLURONIC® 17R4.

EXAMPLE 4

The solution of Example 1 was evaluated using the ISO 14729 Stand Alone Disinfection Efficacy protocols. Three lots of product were each challenged with the 5 panel organisms. The results are put forth in Tables 1–5.

TABLE 1

*Fusarium solani*

| Time Point (hr) | Lot No. 63131 Inoculum Check $3.1 \times 10^5$ | | Lot No. 62423 Inoculum Check $2.9 \times 10^5$ | | Lot No. 81116 Inoculum Check $3.0 \times 10^5$ | | Mean Log Drop for All Lots | |
|---|---|---|---|---|---|---|---|---|
| | Survivors | Log Drop | Survivors | Log Drop | Survivors | Log Drop | Survivors | Log Drop |
| 1.5 | $9.7 \times 10^3$ | 1.5 | $3.5 \times 10^2$ | 2.9 | $3.4 \times 10^3$ | 1.9 | $4.5 \times 10^3$ | 1.8 |
| 3.0 | $4.6 \times 10^3$ | 1.8 | $5.4 \times 10^2$ | 2.7 | $2.7 \times 10^3$ | 2.0 | $2.6 \times 10^3$ | 2.1 |
| 4.5 | $4.1 \times 10^3$ | 1.9 | $1.1 \times 10^2$ | 3.4 | $2.6 \times 10^3$ | 2.1 | $2.3 \times 10^3$ | 2.1 |
| 6.0 | $1.5 \times 10^3$ | 2.3 | $1.2 \times 10^2$ | 3.4 | $1.9 \times 10^3$ | 2.2 | $1.2 \times 10^3$ | 2.4 |
| 24.0 | $2.8 \times 10^2$ | 3.0 | $1.0 \times 10^1$ | 4.5 | $7.0 \times 10^1$ | 3.6 | $1.2 \times 10^2$ | 3.4 |

TABLE 2

*Candida albicans*

| Time Point (hr) | Lot No. 63131 Inoculum Check $2.0 \times 10^5$ | | Lot No. 62423 Inoculum Check $2.8 \times 10^5$ | | Lot No. 81116 Inoculum Check $3.4 \times 10^5$ | | Mean Log Drop for All Lots | |
|---|---|---|---|---|---|---|---|---|
| | Survivors | Log Drop | Survivors | Log Drop | Survivors | Log Drop | Survivors | Log Drop |
| 1.5 | $4.4 \times 10^2$ | 2.7 | $5.3 \times 10^1$ | 3.7 | $4.9 \times 10^2$ | 2.8 | $3.3 \times 10^2$ | 2.9 |
| 3.0 | $9.3 \times 10^1$ | 3.3 | $3.0 \times 10^1$ | 4.0 | $1.8 \times 10^2$ | 3.3 | $1.0 \times 10^2$ | 3.4 |
| 4.5 | $1.1 \times 10^2$ | 3.3 | $2.0 \times 10^1$ | 4.1 | $1.6 \times 10^2$ | 3.3 | $9.7 \times 10^1$ | 3.4 |
| 6.0 | $2.3 \times 10^1$ | 3.9 | <10 | >4.4 | $4.0 \times 10^1$ | 3.9 | $2.1 \times 10^1$ | 4.1 |
| 24.0 | $1.3 \times 10^1$ | 4.2 | <10 | >4.4 | $2.0 \times 10^1$ | 4.2 | $1.1 \times 10^1$ | 4.4 |

TABLE 3

*Serratia marcescens*

| Time Point (hr) | Lot No. 63131 Inoculum Check $3.8 \times 10^5$ | | Lot No. 62423 Inoculum Check $3.9 \times 10^5$ | | Lot No. 81116 Inoculum Check $3.9 \times 10^5$ | | Mean Log Drop for All lots | |
|---|---|---|---|---|---|---|---|---|
| | Survivors | Log Drop | Survivors | Log Drop | Survivors | Log Drop | Survivors | Log Drop |
| 1.5 | <10 | >4.6 | <10 | >4.6 | <10 | >4.6 | <10 | >4.6 |
| 3.0 | <10 | >4.6 | <10 | >4.6 | <10 | >4.6 | <10 | >4.6 |
| 4.5 | <10 | >4.6 | <10 | >4.6 | <10 | >4.6 | <10 | >4.6 |
| 6.0 | <10 | >4.6 | <10 | >4.6 | <10 | >4.6 | <10 | >4.6 |

TABLE 5

*Pseudomonas aeruginosa*

| Time Point (hr) | Lot No. 63131 Inoculum Check $2.6 \times 10^5$ | | Lot No. 62423 Inoculum Check $2.3 \times 10^5$ | | Lot No. 81116 Inoculum Check $3.1 \times 10^5$ | | Mean Log Drop for All lots | |
|---|---|---|---|---|---|---|---|---|
| | Survivors | Log Drop | Survivors | Log Drop | Survivors | Log Drop | Survivors | Log Drop |
| 1.5 | <10 | >4.4 | <10 | >4.4 | <10 | >4.5 | <10 | >4.4 |
| 3.0 | <10 | >4.4 | <10 | >4.4 | <10 | >4.5 | <10 | >4.4 |
| 4.5 | <10 | >4.4 | <10 | >4.4 | <10 | >4.5 | <10 | >4.4 |
| 6.0 | <10 | >4.4 | <10 | >4.4 | <10 | >4.5 | <10 | >4.4 |

TABLE 4

*Staphylococcus aureus*

| Time Point (hr) | Lot No. 63131 Inoculum Check $2.6 \times 10^5$ | | Lot No. 62423 Inoculum Check $3.5 \times 10^5$ | | Lot No. 81116 Inoculum Check $2.5 \times 10^5$ | | Mean Log Drop for All Lots | |
|---|---|---|---|---|---|---|---|---|
| | Survivors | Log Drop | Survivors | Log Drop | Survivors | Log Drop | Survivors | Log Drop |
| 1.5 | $3.3 \times 10^2$ | 2.9 | $1.1 \times 10^2$ | 3.5 | $3.5 \times 10^2$ | 2.9 | $2.6 \times 10^2$ | 3.0 |
| 3.0 | $3.3 \times 10^2$ | 2.9 | $8.0 \times 10^1$ | 3.6 | $3.4 \times 10^2$ | 2.9 | $2.5 \times 10^2$ | 3.1 |
| 4.5 | $1.1 \times 10^2$ | 3.4 | $4.0 \times 10^1$ | 3.9 | $3.1 \times 10^2$ | 2.9 | $1.5 \times 10^2$ | 3.3 |
| 6.0 | $5.3 \times 10^1$ | 3.7 | $2.3 \times 10^1$ | 4.2 | $5.3 \times 10^1$ | 3.7 | $4.3 \times 10^1$ | 3.8 |

EXAMPLE 5

The solution of Example 2 was evaluated using the ISO 14729 Stand Alone Disinfection Efficacy protocols. Three lots of product were each challenged with the 5 panel organisms. The results are put forth in Tables 6–10.

TABLE 6

*Fusarium solani*

| Time Point (hr) | Lot No. 95972 Inoculum Check $1.8 \times 10^5$ | | Lot No. 95973 Inoculum Check $1.6 \times 10^5$ | | Lot No. 95974 Inoculum Check $2.6 \times 10^5$ | | Mean Log Drop for All Lots | |
|---|---|---|---|---|---|---|---|---|
| | Survivors | Log Drop | Survivors | Log Drop | Survivors | Log Drop | Survivors | Log Drop |
| 1.5 | $6.0 \times 10^1$ | 3.5 | $2.0 \times 10^1$ | 3.9 | $3.3 \times 10^1$ | 3.9 | $3.8 \times 10^1$ | 3.8 |
| 3.0 | $3.3 \times 10^1$ | 3.7 | <10 | 4.4 | $3.3 \times 10^1$ | 3.9 | $2.4 \times 10^1$ | 4.0 |
| 4.5 | $2.7 \times 10^1$ | 3.8 | NR | >4.7 | $3.7 \times 10^1$ | 3.9 | $2.2 \times 10^1$ | 4.1 |
| 6.0 | $1.7 \times 10^1$ | 4.0 | NR | >4.7 | NR | >5.4 | <10 | 4.7 |
| 24.0 | <10 | 4.7 | NR | >4.7 | NR | >4.9 | NR | >4.8 |

TABLE 7

*Candida albicans*

| Time Point (hr) | Lot No. 95972 Inoculum Check $3.7 \times 10^5$ | | Lot No. 95973 Inoculum Check $3.4 \times 10^5$ | | Lot No. 95974 Inoculum Check $5.0 \times 10^5$ | | Mean Log Drop for All lots | |
|---|---|---|---|---|---|---|---|---|
| | Survivors | Log Drop | Survivors | Log Drop | Survivors | Log Drop | Survivors | Log Drop |
| 1.5 | NR | >5.0 | NR | >5.0 | NR | >5.2 | NR | >5.1 |
| 3.0 | NR | >5.0 | NR | >5.0 | NR | >5.2 | NR | >5.1 |
| 4.5 | NR | >5.0 | NR | >5.0 | NR | >5.2 | NR | >5.1 |
| 6.0 | NR | >5.0 | NR | >5.0 | NR | >5.2 | NR | >5.1 |
| 24.0 | NR | >5.0 | NR | >5.0 | NR | >5.2 | NR | >5.1 |

TABLE 8

*Serratia marcescens*

| Time Point (hr) | Lot No. 95972 Inoculum Check $1.1 \times 10^6$ | | Lot No. 95973 Inoculum Check $7.3 \times 10^5$ | | Lot No. 95974 Inoculum Check $1.9 \times 10^6$ | | Mean Log Drop for All lots | |
|---|---|---|---|---|---|---|---|---|
| | Survivors | Log Drop | Survivors | Log Drop | Survivors | Log Drop | Survivors | Log Drop |
| 1.5 | NR | >5.5 | NR | >5.8 | NR | >5.8 | NR | >5.8 |
| 3.0 | NR | >5.5 | NR | >5.8 | NR | >5.8 | NR | >5.8 |
| 4.5 | NR | >5.5 | NR | >5.8 | NR | >5.8 | NR | >5.8 |
| 6.0 | NR | >5.5 | NR | >5.8 | NR | >5.8 | NR | >5.8 |

TABLE 9

*Staphylococcus aureus*

| Time Point (hr) | Lot No. 95972 Inoculum Check $2.0 \times 10^6$ | | Lot No. 95973 Inoculum Check $2.0 \times 10^6$ | | Lot No. 95974 Inoculum Check $1.9 \times 10^6$ | | Mean Log Drop for All lots | |
|---|---|---|---|---|---|---|---|---|
| | Survivors | Log Drop | Survivors | Log Drop | Survivors | Log Drop | Survivors | Log Drop |
| 1.5 | NR | >5.8 | NR | >5.8 | NR | >5.8 | NR | >5.8 |
| 3.0 | NR | >5.8 | NR | >5.8 | NR | >5.8 | NR | >5.8 |
| 4.5 | NR | >5.8 | NR | >5.8 | NR | >5.8 | NR | >5.8 |
| 6.0 | NR | >5.8 | NR | >5.8 | NR | >5.8 | NR | >5.8 |

TABLE 10

*Pseudomonas aeruginosa*

| Time Point (hr) | Lot No.95972 Inoculum Check $9.3 \times 10^5$ | | Lot No.95973 Inoculum Check $5.2 \times 10^5$ | | Lot No.95974 Inoculum Check $6.1 \times 10^5$ | | Mean Log Drop for All lots | |
|---|---|---|---|---|---|---|---|---|
| | Survivors | Log Drop | Survivors | Log Drop | Survivors | Log Drop | Survivors | Log Drop |
| 1.5 | NR | >5.5 | NR | >5.2 | NR | >5.3 | NR | >5.3 |
| 3.0 | NR | >5.5 | NR | >5.2 | NR | >5.3 | NR | >5.3 |
| 4.5 | NR | >5.5 | NR | >5.2 | NR | >5.3 | NR | >5.3 |
| 6.0 | NR | >5.5 | NR | >5.2 | NR | >5.3 | NR | >5.3 |

As can be seen above, while the prior art Exemple 1 solution did not achieve total kill against 3 of the panel organisms, the inventive Example 2 solution achieved total kill against all five panel organisms. Thus, the results of Examples 4 and 5 demonstrate the unexpected and surprising benefit that the inventive solution, by achieving a total kill in the disinfection step, may be used in a "no rub-no rinse" regimen of lens care.

EXAMPLE 6

A preservative efficacy test was initiated using the FDA guidelines for multi-dose products. Three lots of the formulation of Example 2 were tested and found to meet the requirements for preservative efficacy with a re-challenge.

EXAMPLE 7 (Comparative)

A study was conducted to compare the protein cleaning efficacies of one solution each from Examples 1, 2, and 3; and two other peroxide systems; namely, EasySEPT One-Step Peroxide system and OXYSEPT 1 STEP (Ultracare Neutralizer/Disinfectant). The solutions of Examples 1, 2, and 3, and the EasySEPT One-Step peroxide system each involved a "no rub/no rinse" 6-hour disinfections and neutralization system.

The study was conducted by an external, independent laboratory (Bio-Concept Laboratories, Inc.) using a Ninhydrin Assay (Bio-Concept Laboratories SOP # TM-00051-01) to compare the remaining protein on the lenses after the regimen to the amount of protein loaded onto soiled lenses.

The results of this study are put forth in Table 6. The protein removal effectiveness shown by the solutions of Examples 2 and 3 showed significantly better cleaning efficacies than EasySEPT One-Step and OXYSEPT 1-STEP.

TABLE 11

| Test Regimen | Protein Concentration μg/lens | Amount of protein removed (%) |
| --- | --- | --- |
| Example 2 "no rub/no rinse" 6-hour disinfection and neutralization | 115 | 29 |
| Example 3 "no rub/no rinse" 6-hour disinfection and neutralization | 108 | 34 |
| Example 1 "no rub/no rinse" 6-hour disinfection and neutralization | 112 | 31 |
| B&L EasySEPT One-Step "no rub/no rinse" 6-hour disinfection and neutralization | 128 | 21 |
| OXYSEPT 1STEP "no rub/no rinse" with tablet 6-hour disinfection and neutralization | 154 | 6 |
| Soiled Lenses (no regimen) | 163 | — |

EXAMPLE 8

Studies were conducted to assess the contact angle of the Example 1 formulation versus the Example 2 formulation on Group I and IV soft contact lenses (FDA categories). Group IV is distinguished from Group I by having higher water content and being more ionic. Typically, Group IV lenses have a water content greater than 50% by weight. The contact angle of phosphate buffered saline was then measured. The second study evaluated the contact angle of "fresh" lenses directly out of the package. The contact angle of both the Example 1 formulation and the Example 2 formulation were measured. The results put forth in Tables 12 and 13 indicate that the formulation of Example 2 has better wetting than Example 1 in both studies.

TABLE 12

| Lens type | Example 2 | Example 1 |
| --- | --- | --- |
| Group IV, vifilcon A | 38 | 66 |
| Group I, tefilcon | 36 | 45 |

TABLE 13

| Lens type | Example 2 | Example 1 |
| --- | --- | --- |
| Group IV, vifilcon A | 43 | 83 |
| Group I, tefilcon | 32 | 60 |

EXAMPLE 9

Shelf life studies were conducted on 3 lots of the formulation of Example 2. The solution was bottled in bottles currently used in the commercial version of the Example 1 formulation (AOSept®). The samples were placed at 25° C., 35° C., and 45° C. The results indicate that the solutions are stable for at least 18 months.

EXAMPLE 10

The following seven solutions were prepared to assess the foaming tendencies of various surfactants:
Solution A=Example 1 (no surfactant)
Solution B=Example 2 (0.05% PLURONIC® 17R4)
Solution C=Example 3 (0.10% PLURONIC® 17R4)
Solution D=Example 1 with 0.01% PLURONIC® F-68LF ("low foaming")
Solution E=Example 1 with 0.02% PLURONIC® F-68LF
Solution F=Example 1 with 0.035% PLURONIC® F-68LF
Solution G=Example 1 with 0.07% PLURONIC® F-68LF Each of the solutions were placed in a separate commonly used disinfection cup (AOCup® with AODisc® and covered with an AOCap®). The AODisc® is a platinum-coated plastic disk that catalytically decomposes the hydrogen peroxide, generating oxygen gas bubbles.

Solutions A, B, and C showed no significant foaming at any time within the disinfection cycle. On the other hand, Solutions E, F, and G all caused foaming and overflow out of the container within 60 seconds; and Solution D caused foaming and overflow within 90 seconds. These results indicate that PLURONIC® F-68LF is not suitable as a surfactant for use in all hydrogen peroxide systems.

The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention. Furthermore, titles, headings, definitions or the like are provided to enhance the reader's comprehension of this document, and should not be read as limiting the scope of the present invention. Accordingly, the intellectual property rights to this invention are defined only by the following claims and reasonable extensions and equivalents thereof.

I claim:

1. A composition for disinfecting a contact lens, comprising
an effective disinfecting amount of hydrogen peroxide and a surfactant comprising a block copolymer of hydrophobe and hydrophile blocks of the structure:

$$HO\text{-}(hydrophobe)_x\text{-}(hydrophile)_y\text{-}(hydrophobe)_x\text{-}H$$

wherein x and y are integers reflecting the respective hydrophile and hydrophobe blocks of said copolymer, and the hydrophile component of the block copolymer constitutes less than 50 weight percent of the block; and being characterized by being incapable of foaming at any time within a disinfection cycle carried out in a disinfection cup having a platinum-coated plastic disk that catalytically decomposes hydrogen peroxide generating oxygen gas bubbles, so significantly to cause overflow of the composition from the disinfection cup.

2. A composition for disinfecting a contact lens as claimed in claim 1, wherein said hydrophile is polyoxyethylene.

3. A composition for disinfecting a contact lens as claimed in claim 2, wherein said hydrophobe is polyoxypropylene.

4. A composition for disinfecting a contact lens as claimed in claim 3, wherein said block copolymer has a Ross-Miles foam height (ASTM designation D-1173-53; 0.1%, at 50° C.) of less than 1 mm.

5. A composition for disinfecting a contact lens as claimed in claim 4, wherein said block copolymer has a Ross-Miles foam height (ASTM designation D-1173-53; 0.1%, at 50° C.) of about 0 mm.

6. A composition for disinfecting a contact lens as claimed in claim 1, wherein the hydrophile constitutes from about 10 to 50 weight percent of the block copolymer.

7. A composition for disinfecting a contact lens as claimed in claim 6, wherein the hydrophile constitutes about 40 weight percent of the block copolymer.

8. A composition for disinfecting a contact lens as claimed in claim 1, wherein the molecular weight of the hydrophobe block is from about 1200 and about 3100.

9. A composition for disinfecting a contact lens as claimed in claim 8, wherein the molecular weight of the hydrophobe is from about 1000 and about 2500.

10. A composition for disinfecting a contact lens as claimed in claim 9, wherein the molecular weight of the hydrophobe is approximately 1700.

11. A composition for disinfecting a contact lens as claimed in claim 1, wherein said surfactant is present in the range of about 0.005% to about 0.8%.

12. A composition for disinfecting a contact lens as claimed in claim 11, wherein said surfactant is present in the range of about 0.01% to about 0.5%.

13. A composition for disinfecting a contact lens as claimed in claim 12, wherein said surfactant is less than 0.1% by weight of the solution.

14. A composition for disinfecting a contact lens comprising an aqueous solution of an effective disinfecting amount of hydrogen peroxide and a polyoxyethylene/polyoxypropylene block copolymer having the structure:

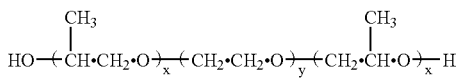

wherein x and y are integers reflecting the respective polyethylene oxide and polypropylene oxide blocks of said copolymer; and the polyoxyethylene component of the block copolymer constitutes less than 50 weight percent of the block copolymer;

wherein said block copolymer has a Ross-Miles foam height (ASTM designation D-1173-53; 0.1%, at 50° C.) of less than 1 mm.

15. A composition for disinfecting a contact lens as claimed in claim 14, wherein said block copolymer has a Ross-Miles foam height (ASTM designation D-1173-53; 0.1%, at 50° C.) of about 0 mm.

16. A composition for disinfecting a contact lens as claimed in claim 15, wherein the polyoxyethylene component of the block copolymer constitutes about 40 weight percent of the block copolymer.

17. A composition for disinfecting a contact lens as claimed in claim 14, wherein the molecular weight of the polyoxypropylene block is from about 1200 and about 3100.

18. A composition for disinfecting a contact lens as claimed in claim 17, wherein the molecular weight of the polyoxypropylene block is approximately 1700.

19. A composition for disinfecting a contact lens as claimed in claim 14, wherein said surfactant is present in the range of about 0.005% to about 0.8%.

20. A composition for disinfecting a contact lens as claimed in claim 21, wherein said surfactant is less than 0.1% by weight of the solution.

21. A composition for disinfecting a contact lens as claimed in claim 14, wherein hydrogen peroxide is present in a concentration of about 0.5% to about 6% by weight.

22. A composition for disinfecting a contact lens as claimed in claim 21, wherein hydrogen peroxide is present in a concentration of 2% to 6% by weight.

23. A composition for disinfecting a contact lens as claimed in claim 21, further comprising a hydrogen peroxide stabilizer; wherein said stabilizer comprises a diphosphonic acid alkanol.

24. A composition for disinfecting a contact lens as claimed in claim 23, wherein said stabilizer comprises diethylene triamine penta-(methylenephosphonic acid) or a occularly compatible salt thereof; wherein said stabilizer is about 0.006 and about 0.02% by weight of the composition.

25. A composition for disinfecting a contact lens as claimed in claim 22, further comprising a buffer to maintain said composition at a pH of about 4 to about 9.

26. A composition for disinfecting a contact lens as claimed in claim 25, wherein said buffer is selected from the group consisting of basic acetates, phosphates, borates, nitrates, sulfates, tartrates, lactates, carbonates, bicarbonates, and mixtures thereof; wherein said buffer is present in the range of 0.001% to 2%.

27. A composition for disinfecting a contact lens as claimed in claim 26, wherein said phosphate buffer is selected from the group consisting of monobasic phosphates, dibasic phosphates, and mixtures thereof; wherein said phosphate buffer is present in the range of from about 0.05% to about 0.30%.

28. A composition for disinfecting a contact lens as claimed in claim 27, further comprising a tonicity component to provide the solution with a tonicity of from 50 to 400 mosmol/kg; wherein said tonicity component is selected from the group consisting of water soluble salts compatible with ocular tissue.

29. A composition for disinfecting a contact lens comprising an aqueous solution of:
an effective disinfecting amount of hydrogen peroxide;
a buffer compatible with ocular tissue;
a hydrogen peroxide stabilizer comprising a diphosphonic acid alkanol;
a tonicity component; and
polyoxyethylene/polyoxypropylene block copolymer having the structure:

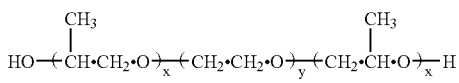

wherein x and y are integers reflecting the respective polyethylene oxide and polypropylene oxide blocks of said copolymer, wherein said block copolymer has a Ross-Miles foam height (ASTM designation D-1173-53; 0.1%, at 50° C.) of less than 1 mm.

30. A composition for disinfecting a contact lens as claimed in claim 29, wherein said block copolymer has a Ross-Miles foam height (ASTM designation D-1173-53; 0.1%, at 50° C.) of about 0 mm.

31. A composition for disinfecting a contact lens as claimed in claim 30, wherein the polyoxyethylene component of the block copolymer constitutes less than 50 weight percent of the block copolymer.

32. A composition for disinfecting a contact lens as claimed in claim 30, wherein said stabilizer comprises diethylene triamine penta-(methylenephosphonic acid) or a occularly compatible salt thereof and is present in the composition in an amount between about 0.001 and about 0.03% by weight of the solution.

33. A composition for disinfecting a contact lens as claimed in claim 30, wherein said buffer is selected from the group consisting of sodium dibasic phosphate ($Na_2HPO_4$), sodium monobasic phosphate ($NaH_2PO_4$), potassium monobasic phosphate ($KH_2PO_4$), and mixtures thereof; and said phosphate buffer is present in the range of from about 0.05% to about 0.30%.

34. A composition for disinfecting a contact lens as claimed in claim 30, wherein said tonicity component is sodium chloride and provides said solution with a tonicity of from 250 to 350 mosmol/kg.

35. A composition for disinfecting a contact lens as claimed in claim 29, comprising from 2 to 6% hydrogen peroxide; and between 0.01% and 0.10% polyoxyethylene/polyoxypropylene block copolymer;

wherein the polyoxyethylene component of the block copolymer constitutes about 40 weight percent of the block copolymer; and wherein the molecular weight of the polyoxypropylene block of the copolymer is approximately 1700.

36. A method of disinfecting a contact lens comprising the steps of:

(a) contacting a contact lens with an aqueous solution of an effective disinfecting amount of hydrogen peroxide and a polyoxyethylene/polyoxypropylene block copolymer having the structure:

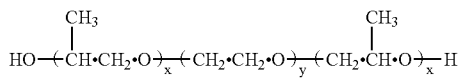

wherein x and y are integers reflecting the respective polyethylene oxide and polypropylene oxide blocks of said copolymer; and the polyoxyethylene component of the block copolymer constitutes less than 50 weight percent of the block copolymer;

wherein said block copolymer has a Ross-Miles foam height (ASTM designation D-1173-53; 0.1%, at 50° C.) of less than 1 mm; and (b) neutralizing said hydrogen peroxide by catalytic decomposition.

37. A method of disinfecting a contact lens as claimed in claim 36, wherein said step of neutralizing comprises contacting said solution with a metal catalyst.

38. A method of disinfecting a contact lens as claimed in claim 37, wherein the lens is ready for insertion into the eye without a step of manually rubbing the lens.

* * * * *